United States Patent [19]

Joslin

[11] Patent Number: 5,792,083

[45] Date of Patent: Aug. 11, 1998

[54] ARM SLING

[76] Inventor: Marianne Joslin, 50 California St. Suite 1500, San Francisco, Calif. 94111

[21] Appl. No.: 665,271

[22] Filed: Jun. 17, 1996

[51] Int. Cl.$^6$ .................................................. A61F 5/40
[52] U.S. Cl. ................................ 602/4; 602/5; 602/62
[58] Field of Search ......................... 602/4, 5, 60–62; 178/877, 878; 224/159, 160, 254

[56] References Cited

U.S. PATENT DOCUMENTS

| | | | |
|---|---|---|---|
| 3,327,914 | 6/1967 | Abram | 224/159 |
| 4,285,337 | 8/1981 | Cosentino | 602/4 |
| 4,622,961 | 11/1986 | Christensen | 602/4 |
| 4,691,917 | 9/1987 | Battista | 482/126 |
| 4,759,353 | 7/1988 | Melendez | 602/4 |
| 4,834,082 | 5/1989 | Ghadiali | 602/4 |
| 4,895,142 | 1/1990 | Liptak | 602/4 |
| 5,071,047 | 12/1991 | Cordisco | 224/159 X |
| 5,086,762 | 2/1992 | Chee | 602/4 |

*Primary Examiner*—Richard J. Apley
*Assistant Examiner*—Denise Pothier
*Attorney, Agent, or Firm*—Townsend and Townsend and Crew

[57] ABSTRACT

A longitudinally symmetric arm sling for supporting a forearm of a person has first and second substantially identical panel sections which are sewn to each other so that the sections define a trough with a closed aft end and an open front end into which the arm can be placed. A single strap has a first end attached to the aft end of the panel sections and a second end attached to the front end of the panel sections so that portions of the strap and of the panel sections adjacent the front end define opposing openings into which a thumb can be extended irrespective of whether the sling is worn on a right arm or a left arm. The strip is relatively wide and sewn to the panel sections so that wide sides of the strip are parallel to the panel sections. The sling and the strap are constructed of a relatively soft, stretchable material. A buckle can be provided to make the strap length adjustable.

18 Claims, 2 Drawing Sheets

ARM SLING

BACKGROUND OF THE INVENTION

This invention relates to slings for optionally supporting a person's left or right arm.

Arm slings are extensively used whenever a person must protect and/or support his or her arm following an injury or sickness. A variety of arm slings is currently available on the market, and an even larger number of sling designs is known in the art as is exemplified, for example, by U.S. Pat. Nos. 2,594,809 and 4,285,337. Such arm slings have the common characteristic of forming a pouch into which the person's forearm can be placed so that his hand extends partially or fully from a front end of the pouch. A strap secured to the pouch adjacent its front and aft ends is slung over the person's shoulder so that the weight of the arm is supported by the pouch and the strap while the arm is kept in a protected manner close to the person's torso.

Typically, the pouches of prior art arm slings have a closed aft end and the strap, which is relatively wide to avoid undue pressure when it is draped over the person's shoulder and carries the weight of the arm, is secured, e.g. sewn, to an aft wall of the pouch which is oriented transversely to side panels of the pouch. The other end of the strap is suitably secured to the front end of the pouch, often with buckles, pins and the like, to facilitate the application of the arm sling and make the strap adjustable in length. The pouches and/or straps are frequently made of relatively stiff and strong material to render them more rigid, a feature which is at times enhanced by incorporating stiffening plates or the like into portions of the panel such as, for example, its lower base.

Prior art arm slings are fully capable of supporting the person's arm and frequently provide a degree of protection for the arm as well. By virtue of their construction they are, however, not longitudinally symmetrical and/or are not identical when worn on the left or right arm. Further, they are relatively complex and, therefore, costly to produce. Moreover, when not in use, such slings are bulky and impractical to store in a small place and/or carry around; for example, in one's pocket for use when needed.

SUMMARY OF THE INVENTION

The present invention provides a simple, practical and lightweight arm sling which can be folded into a small package, not much bigger than a folded handkerchief, when not in use. The sling is longitudinally symmetric so that it can be applied identically to the left or right arm. It can be made of inexpensive materials and requires minimal labor to produce so that it can be economically produced. Additionally, the sling is ideally adapted to be made of attractive materials such as fabrics having pleasant colors, designs and/or patterns, in distinction to the commonly utilitarian and drab-looking slings in current use.

Generally speaking, an arm sling constructed in accordance with the present invention is made of two elongated panels of a soft fabric, such as a stretchable webbing, which are sewn together face-to-face along a seam which extends from a front end of the panels to the aft ends thereof. In a presently preferred embodiment, a single strap of the desired width has a first end which is disposed between opposing sides of the two panels adjacent their aft ends and, therefore, is parallel to the panels. A second end of the strap defines a front loop which extends parallel to the panels at the front ends thereof and is sewn thereto at three spaced-apart locations to define openings between each panel section and the overlying portion of the strap for anchoring the sling to the person's hand to prevent slippage during use. The entire strap is essentially parallel to the panels when the latter are placed flat-to-flat against each other.

In use, the panels are spread apart to define a trough or pouch into which the person's forearm can be placed. The strap is slung over the person's shoulder to support the arm in the pouch.

To prevent the sling from sliding back along the person's arm during use, the person's thumb is extended through one or the other of the openings defined by the portions of the strap which overlie the front ends of the panels.

Since the strap is parallel to the panels (when placed flat against each other) and a thumb opening is provided at the front end on either side of the pouch, the sling is symmetrical about its longitudinal center plane and can equally well be worn on the left arm or the right arm.

In a presently preferred embodiment of the invention, the panels and the straps are constructed of the same, soft and pliable material, which, in addition, is preferably stretchable, such as the stretch material available on the market under the trademark "Lycra". Such materials are mass-produced in many attractive colors, designs and patterns and they are available at reasonable costs. The material is soft so that it is readily assembled into a sling by cutting the panels and the straps from a sheet of such material and then sewing them together to form the arm sling of the present invention.

Since the sling requires no hardware and is readily foldable, it can be folded into a small package only marginally larger than a folded handkerchief for storage and nonuse and can, for example, be carried in garment pockets.

From the point of view of the manufacturer, since the arm sling is entirely sewn, it will typically be made available in several sizes; say, small, medium and large. By using stretchable material, such as Lycra fabric, the sling can stretch or contract to some extent over a limited range. This reduces the number of different sling sizes that must be made available to the general population and/or enhances the fit of the sling.

As a result, the sling of the present invention is practical to use, economical to make, and can be sold at a relatively low price.

Of course, if desired, a simple, small buckle can be included in the strap to make its length adjustable.

DESCRIPTION OF THE PREFERRED EMBODIMENTS

Figure 1:
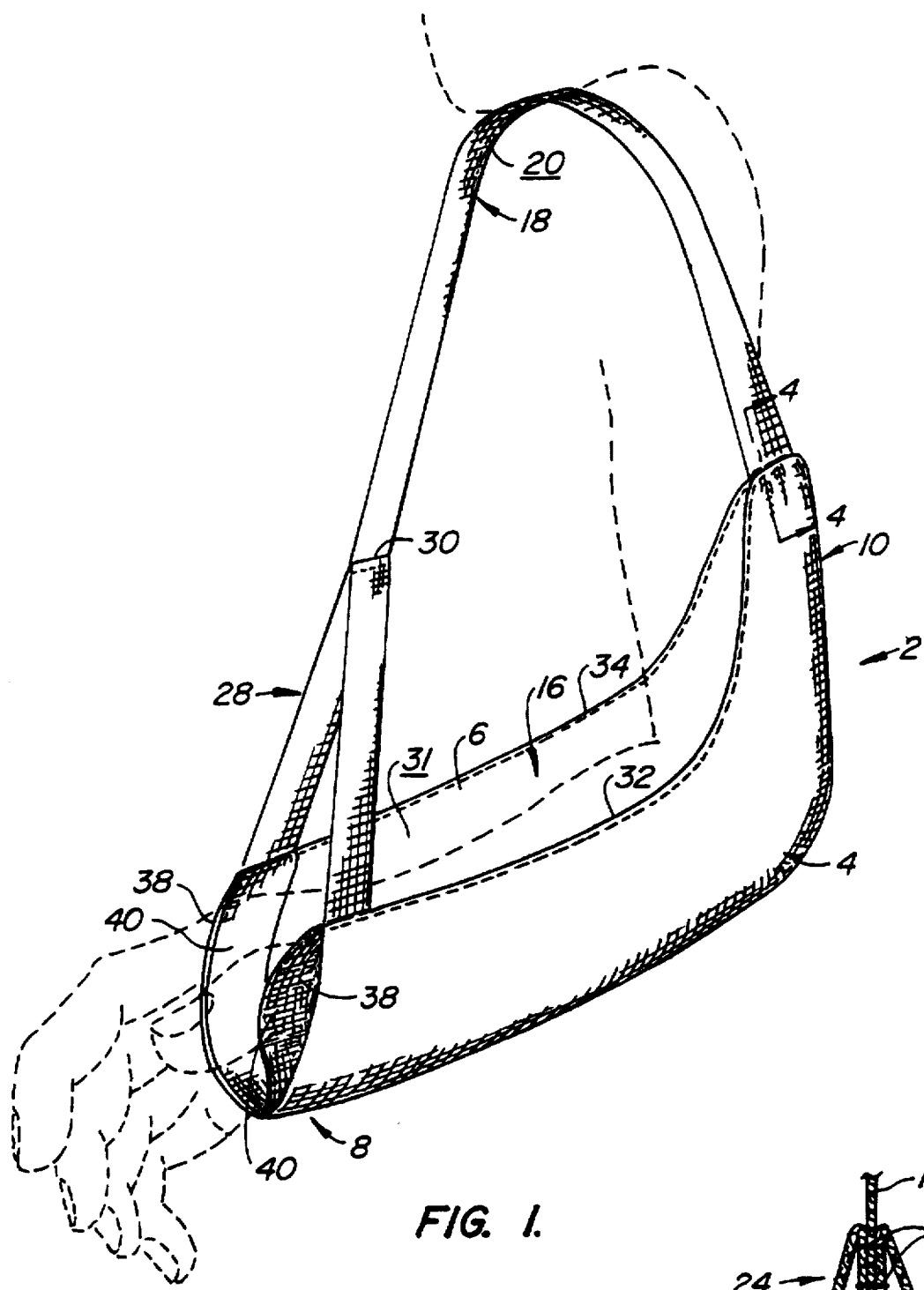
FIG. 1 is a perspective, front elevational view which shows the arm sling of the present invention supporting an arm (shown in phantom lines) of a person.
Figure 4:
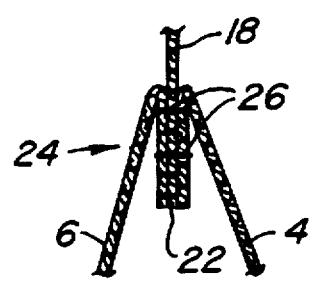
FIG. 4 is a partial, front elevational view in section and is taken on line 4—4 of FIG. 1.

Referring to the drawings, the arm sling 2 of the present invention is made of first and second, identically shaped, elongated panel sections 4, 6 which extend from a front end 8 of the sections to an aft end 10 thereof. Common lower and aft edges 12, 14 of the panel sections are stitched together so that the panel sections can be expanded, as is shown in FIG. 1, into an upwardly and forwardly open, and downwardly and rearwardly closed trough or pouch 16.

A relatively wide strap 18 has wide sides 20, an one end 22 sandwiched between panel sections 4, 6 at an upper portion 24 of the aft end of the sections, and is secured thereto by stitching 26.

At the front end 8, strap 18 forms a loop 28 by doubling over a portion of the strap and attaching, e.g. sewing, the other end 30 of the strap to the remainder of the strap as is best seen in FIG. 1. A portion of the loop is placed against inner sides 31 of panel sections 4, 6 and attached, e.g. sewn, thereto adjacent upper edges 32, 34 of the panel sections to secure the strap and the panel sections to each other. The portion of the loop fitted against the sides of the panels which face each other is further secured to the panel sections at at least one additional location; for example, in the vicinity of lower panel edges 12. As a result, loose strap parts 40 of the strap which overlie the inside surfaces of the panel sections can be lifted, as is illustrated in FIG. 1, to define openings 38, one each overlying each of the two panel sections.

Figures 2, 3:
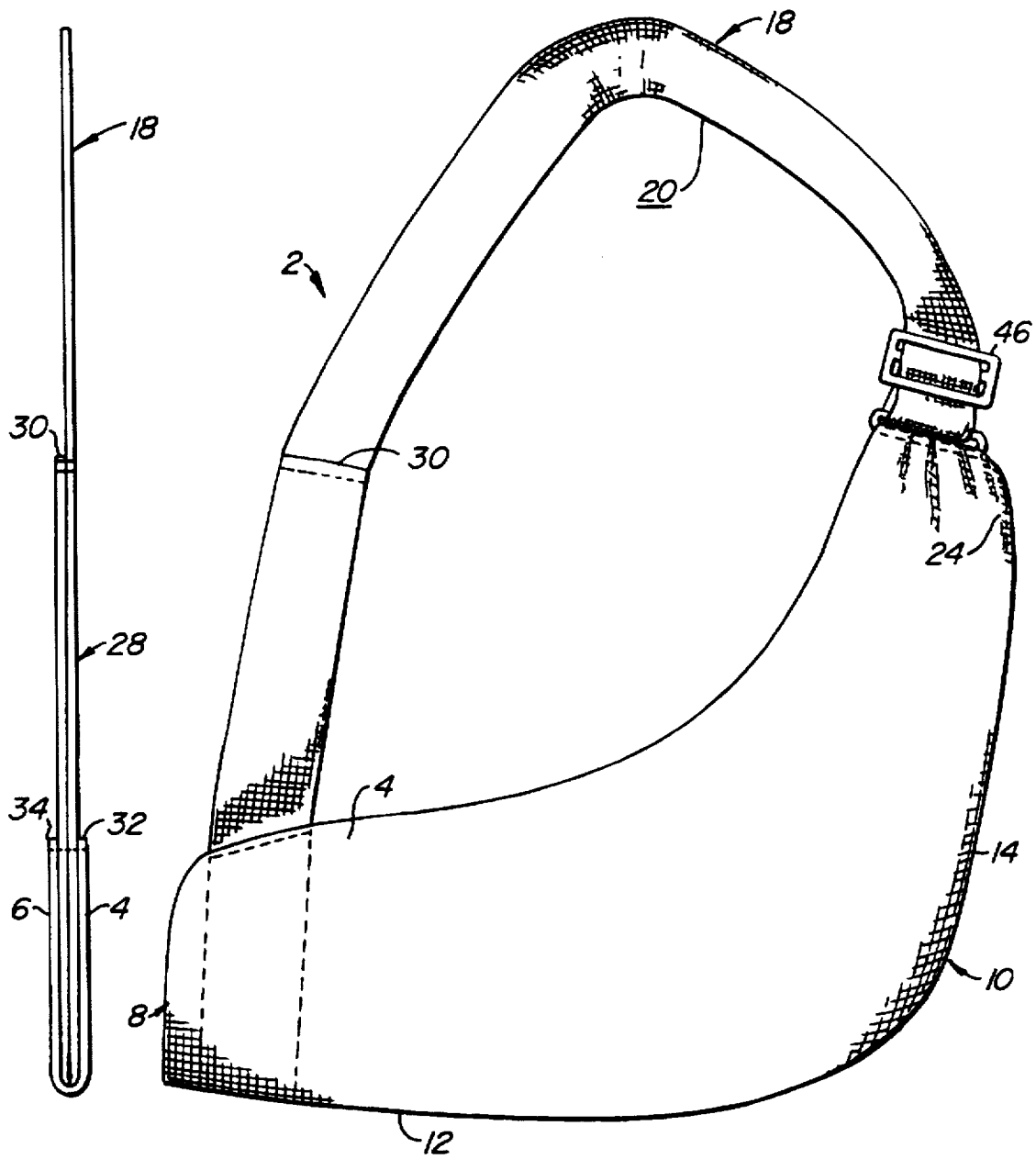
FIG. 2 is a side elevational view of a modified form of the arm sling in its collapsed position in which panels of the sling lie substantially flat face-to-face against each other.
FIG. 3 is a front elevational view of the folded sling shown in FIG. 1.

The arm sling is symmetrical about a vertical plane extending over the length of the panels and intersecting the lower edge 12 of the pouch (FIG. 2). As a result, when the arm is placed in the pouch of the sling and loop 28 is spread open as illustrated in FIG. 1 it can equally be used to support the right or the left arm.

The panel sections 4, 6 and strap 18 are constructed of the same, soft, pliable and preferable stretchable material, such as Lycra webbing.

Following the manufacture of arm sling 2, the panel sections are folded face-to-face flat against each other, as is illustrated in FIGS. 2 and 3, strap 18 is doubled over so that it overlies the panel sections, and the panel sections and the strap are then together folded into a small package for storage and shipment. The package is of such small size that it is readily placed in most garment pockets.

When the arm sling of the present invention is to be used, it is unfolded and the panel sections are spread apart into the configuration illustrated in FIG. 1 to form trough 16. The strap is slung over the person's shoulder and his or her forearm is placed into the trough as is illustrated in phantom lines in FIG. 1. When placing the arm into the trough, one or the other loose strap parts 40 is lifted to form opening 38 and the person's thumb is extended through the opening, as is also illustrated in FIG. 1. Arm sling 2 now supports the weight of the arm from the person's shoulder and the thumb engages strap part 40 and anchors the sling to the person's hand so that the sling cannot slide backwardly along the person's arm during use.

Referring now to FIG. 2, to make strap 18 of adjustable length, the strap is secured to the front end 8 of the sling as previously described. A buckle 46 of conventional construction is carried by the strap in the vicinity of its aft end. The free end portion of the strap is extended through the buckle and appropriately attached thereto, by means of a friction fit or a clasp (not shown) after the desired overall strap length has been set. In all other respects, an arm sling which includes a strap length adjustment buckle is constructed and used as described above.

What is claimed is:

1. An elongated arm sling comprising a panel constructed of a soft material having an aft end and an open front end and first and second panel sections which define a trough between them into which a person's forearm can be placed, the panel sections being foldable flat face-to-face during nonuse of the sling, and a single, continuous strap having strap segments attached to the panel at the front and aft ends, the strap having wide sides and wide sides of the strap and the strap segments being parallel to the panel sections when the panel sections are folded flat face-to-face, the strap including a first part which extends along at least a portion of at least one of the panel sections adjacent the front end of the panel and on a side of the panel section facing the other one of the panel sections, and wherein the part of the strap and the one of the panel sections define an opening into which a thumb of the person can be extended during use of the sling.

2. An arm sling according to claim 1 wherein the panel sections are defined by first and second pieces of the material which are attached to each other along respective longitudinal edges of the pieces which are located at about a midportion of the panel.

3. An arm sling according to claim 1 wherein the strap includes a second part attached to the other one of the panel sections and attached thereto so that a side of the other one of the panel sections and the second part define a further opening into which the other thumb of the person can be extended, whereby the sling can alternatively be worn on a left arm and a right arm of the person and permits insertion of a thumb into the corresponding opening defined by the strap and the panel sections.

4. An arm sling according to claim 3 wherein the strap defines a loop adjacent the front end which forms the first and second strap parts that define the thumb openings, the loop extending from a point on the strap intermediate its ends and spaced from proximate edges of the panel along and substantially parallel to the panel adjacent the front end thereof so that the person's hand extends through the loop when the sling is worn by the person.

5. An arm sling according to claim 4 wherein a free end of the strap proximate the loop is attached to a remainder of the strap at the point, and wherein the loop is attached to the panel adjacent the proximate edges of the panel and at a location proximate a midportion of the panel.

6. An arm sling according to claim 5 wherein the panel is made of a stretchable fabric.

7. An arm sling according to claim 6 wherein the strap and the panel are made of the same material.

8. An arm sling according to claim 5 including a buckle operatively connected with the strap for changing an effective length of the strap.

9. An arm sling according to claim 1 wherein the sling is symmetrical about a longitudinal center plane of the sling.

10. An arm sling comprising a panel constructed of a soft fabric having first and second, substantially like shaped panels foldable flat against each other during nonuse of the sling, defining an open front end and a closed aft end of the sling and being expandable to define an upwardly open trough into which a forearm of a person can be placed for support by the sling, an elongated strap formed for hanging the sling over the person's shoulder and having wide sides, a first end of the strap being connected to the panels adjacent the aft end of the sling so that the wide sides of the strap are parallel to the panels when the panels are folded flat against each other, a portion of the strap at a second end thereof defining a loop positioned adjacent the front end of the panels, means securing the loop to the front end of the panels at spaced-apart locations so that segments of the wide sides of the strap which overlie the front ends of the panels are substantially parallel to the panels and each of the panels adjacent the front end in combination with one of the segments of the strap define first and second openings through which the person can extend either thumb so that the person can optionally use the sling on a left or a right arm while extending a thumb through an appropriate one of the first and second openings, and means securing the second end of the strap to a remainder of the strap at a location spaced from the ends of the strap.

11. An arm sling according to claim 10 including means for securing the loop of the strap to the panel sections at first, second and third spaced-apart locations so that parts of the strap between the first, second and third locations define portions of the openings.

12. An arm sling according to claim 10 including means securing the panel sections to each other along a seam extending from the front end to the aft end of the panel sections.

13. An arm sling according to claim 10 wherein the panel sections are constructed of a one-piece fabric.

14. An arm sling according to claim 13 wherein the strap comprises a single strap which is connected to the panel sections with stitching.

15. An arm sling according to claim 10 wherein the strap is a single strap.

16. An arm sling according to claim 10 wherein the panels and the strap are constructed of the same fabric.

17. An arm sling according to claim 11 wherein the fabric comprises a stretchable fabric.

18. An arm sling according to claim 10 wherein the sling is symmetrical about a longitudinal center plane of the sling.

* * * * *